(12) United States Patent
Evans et al.

(10) Patent No.: US 8,187,441 B2
(45) Date of Patent: May 29, 2012

(54) ELECTROCHEMICAL PUMP

(76) Inventors: Christine E. Evans, Fayetteville, AR (US); Forrest W. Payne, Fayetteville, AR (US); Carl A. Koval, Arvada, CO (US); Richard D. Noble, Boulder, CO (US); Mya A. Norman, Springdale, AR (US)

(*) Notice: Subject to any disclaimer, the term of this patent is extended or adjusted under 35 U.S.C. 154(b) by 307 days.

(21) Appl. No.: 12/546,826

(22) Filed: Aug. 25, 2009

(65) Prior Publication Data

US 2009/0308752 A1     Dec. 17, 2009

Related U.S. Application Data

(63) Continuation-in-part of application No. 11/252,981, filed on Oct. 18, 2005, now Pat. No. 7,718,047.

(60) Provisional application No. 60/620,457, filed on Oct. 19, 2004.

(51) Int. Cl.
*B01D 61/42* (2006.01)
*B01D 69/00* (2006.01)

(52) U.S. Cl. ..................... 204/518; 204/627

(58) Field of Classification Search .......... 204/518, 204/627; 417/48–50, 313; 137/13, 803, 137/15.18; 251/129.01–129.08
See application file for complete search history.

(56) References Cited

U.S. PATENT DOCUMENTS

| | | | | |
|---|---|---|---|---|
| 4,402,817 A * | 9/1983 | Maget | ............................ | 204/265 |
| 4,687,423 A * | 8/1987 | Maget et al. | .................. | 417/379 |
| 5,038,821 A * | 8/1991 | Maget | ............................ | 137/486 |
| 7,559,356 B2 * | 7/2009 | Paul et al. | ...................... | 165/267 |
| 2003/0064507 A1 * | 4/2003 | Gallagher et al. | ......... | 435/287.2 |
| 2004/0072375 A1 * | 4/2004 | Gjerde et al. | ................. | 436/541 |
| 2004/0126890 A1 * | 7/2004 | Gjerde et al. | ................. | 436/53 |
| 2004/0144646 A1 * | 7/2004 | Theeuwes et al. | ............ | 204/450 |
| 2006/0254913 A1 * | 11/2006 | Myers et al. | ................... | 204/450 |

* cited by examiner

*Primary Examiner* — J. Christopher Ball
(74) *Attorney, Agent, or Firm* — J. Charles Dougherty

(57) ABSTRACT

The invention provides electrochemically-based methods and devices for producing fluid flow and/or changes in fluid pressure. In the methods and devices of the invention, current passes through a divided electrochemical cell. Adjacent compartments of the cell are divided by an ionically conducting separator. Each compartment includes an electrode and an electrolyte solution or ionic liquid. The electrolyte solution(s) or ionic liquid(s) and the ionically conducting separator are selected to obtain the desired relationship between the current through the cell and the fluid flowrate and/or change in fluid pressure.

37 Claims, 6 Drawing Sheets

ELECTROCHEMICAL PUMP

CROSS-REFERENCE TO RELATED APPLICATIONS

This continuation-in-part application claims the benefit of U.S. Utility application Ser. No. 11/252,981, filed Oct. 18, 2005, which in turn claims the benefit of U.S. Provisional Application No. 60/620,457, filed Oct. 19, 2004. Each of these applications is hereby incorporated by reference in their entirety.

ACKNOWLEDGEMENT OF GOVERNMENT SUPPORT

This invention was made in part under National Science Foundation grants #0740371 and #0848253. The United States Government has certain rights in this invention.

BACKGROUND OF THE INVENTION

The invention is in the field of electrochemical pumping of fluids, including electrochemical pumps and methods for inducing pressurization and/or flow of fluids.

Pressurization and manipulation of fluids on the nano- and micro-scale are required for a wide range of microfluidics applications, including analytical and synthetic "lab-on-a-chip", ultra-small particle handling, and micro/nano-spray systems. Identical demands are key for smart structures and morphing technologies that incorporate plant-like nastic structures and/or individually addressable cells (Chopra, I., Amer. Inst. Aeronautics Astronautics J. 2002, 40, 2145; Loewy, R. G., Smart. Mater. Struct. 1997, 6, R11). A variety of micropumps have been developed for these applications. One classification system identifies micropumps as either displacement pumps or dynamic pumps (Laser, D. J. and Santiago, J. G., 2004, J. Micromech. Microeng., 14, R35-R64). Displacement pumps exert pressure forces on the working fluid through one or more moving boundaries. Dynamic pumps continuously add energy to the working fluid in a manner that increases either its momentum or its pressure directly and include ultrasonic, magnetohydrodynamic (MHD), electrohydrodynamic (EHD), electroosmotic or electrochemical actuation mechanisms.

Electrokinetic pumps produce fluid flow through electro-osmosis. In these pumps, a dielectric surface is placed in contact with an electrolyte and an electrically charged diffuse layer extends from the solid-liquid interface into the bulk of the electrolyte. The application of an electric potential to an electrolyte in contact with the dielectric surface produces a net force on the diffuse layer. U.S. Pat. No. 6,572,749, to Paul et al., describes an electrokinetic pump comprising at least one tube or channel forming a fluid passageway containing an electrolyte and having a porous dielectric medium disposed therein between one or more spaced electrodes. An electric potential is applied between the electrodes to cause the electrolyte to move in the microchannel by electro-osmotic flow. Silica particles having a diameter of about 100 nm to 6 microns are described as suitable for use as the porous dielectric medium. An ultra micro-porous material such as Vycor® porous glass or a Nafion® membrane was interposed between the electrode and the high-pressure fluid junction. These ultra micro-porous materials are described as capable of carrying current but having pores sufficiently fine that pressure-driven or electro-osmotic flow is negligible. It may be noted that there is some debate in the literature concerning the nano-scale structure of Nafion® material, although it is generally considered to have an effective or equivalent pore diameter of about 4 nm that is conditioning and counter-ion dependent (Mauritz, K. A. and Moore, R. B., 2004, Chem. Rev., 104, 4535-4585; Evans, C. E., Noble, R. D., Nazeri-Thompson, S., Nazeri, B., Koval, C. A., 2006, J. Membrane Sci., 279, 521-528).

The scientific literature describes micro-injectors and micro-dosing systems based on electrolytic gas generation. Lee et al. describe a micro injector actuated by bubbles generating by the boiling or electrolysis of an electrolyte in an actuator chamber (Lee, S. W. et al., 1998, Proc. 11th Annual Int. Workshop on Micro Electro Mechanical Systems, Heidelberg, Piscataway, N.J., IEEE). Böhm et al. describe a micromachined dosing system in which the driving force to dispense liquids originates from the electrochemical generation of gas bubbles by the electrolysis of water (Böhm, S. et al., 2000, J. Micromech. Microeng., 10, 498-504).

U.S. Pat. No. 4,118,299, to Maget, describes an electrochemical water desalination process relying on transport of protons and water through a cation exchange membrane. A salt-containing water stream is mixed with hydrogen and then pumped into an electrochemical cell whose anode and cathode are separated by a cation exchange membrane. The electrochemical cell ionizes hydrogen into protons which migrate to the counter electrode under the influence of an applied potential. The migrating protons entrain liquid water. At the counter-electrode, the migrating protons recombine to form hydrogen while releasing liquid water.

Redox batteries and fuel cells typically involve electrochemical cell compartments, each compartment containing one or more redox couples. The compartments are separated in some cases by an ion selective membrane. Several forms of redox fuel cells or batteries have been developed. U.S. Pat. No. 3,996,064 to Thaller describes a two-compartment cell. During passage of current through the cell, an anode fluid is directed through the first compartment at the same time that a cathode fluid is directed through the second compartment. Chloride salts in aqueous solution are described as useful anode and cathode fluids. U.S. Pat. No. 4,786,567 to Skyllas-Kazacos et al. describes vanadium redox batteries which employ V(V)/(IV) and V(III)/V(II) redox couples.

Finally, the art also includes pumps having a flexible diaphragm that can be used as reciprocating displacement micropumps. Reciprocating displacement micropumps are those in which moving surfaces do pressure work in a periodic manner. Several such pumps are described by Laser and Santiago (Laser, J. and Santiago, J. G., 2004, J. Micromech. Microeng., 14, R35-R64) Typically, a reciprocating displacement micropump comprises a pump chamber bounded on one side by the pump diaphragm, an actuator mechanism or driver, and two passive check valves, one check valve at the inlet (or suction side) and one at the outlet (or discharge side). As the pump diaphragm is oscillated, fluid is discharged on the "out stroke" and fluid is pulled into the pump on the "in stroke." Typical oscillation frequencies range from 1 to 5000 Hz.

There remains a need in the art for additional devices and methods for producing fluid flow and/or pressurization using electrochemical means.

SUMMARY OF THE INVENTION

The invention provides electrochemically-based methods and devices for producing fluid flow and/or changes in fluid pressure. The electrochemical pumps of the invention produce changes in the pressure and/or volume of the electrolyte solution or ionic liquid associated with at least one compartment of an electrochemical cell. These pressure and/or volume changes can then be used to drive flow of the electrolyte solution or ionic liquid or flow of an entirely different fluid. These pressure or volume changes may be positive or negative.

In the methods and devices of the invention, current is passed through a divided electrochemical cell. Adjacent compartments of the cell are divided by an ionically conducting separator. In an embodiment the ionically conducting separator is an ionically conducting membrane. Each compartment includes an electrode and an electrolyte solution or ionic liquid in contact with the electrode. The electrolyte solution(s) or ionic liquid(s) and the ionically conducting separator are selected to obtain the desired relationship between the current through the cell and the fluid flow rate and/or change in fluid pressure. In certain embodiments, the effective or equivalent pore diameter of the ionically conducting membrane is up to about 50 nm, in other embodiments up to about 20 nm, and in other embodiments up to about 4 nm.

The devices of the invention can be sized to produce a variety of flow rates. In different embodiments, the flow rate is between about 0.01 nL/min to about 10 nL/min, or between about 1 nL/min to about 10 µL/min, or between about 1 µL/min to about 1 mL/min. In an embodiment, only modest voltage/current conditions are required to produce flow. Some embodiments of the invention require no moving mechanical parts.

In certain embodiments, forward and reverse pumping are readily available by changing the direction of the current through the electrochemical cell. Flexibility in changing the pumping direction allows repeat sampling and multi-pass processes. The ability to abruptly change the flow direction can aid in fluid mixing.

Each electrolyte solution or ionic liquid comprises a redox couple, i.e. soluble chemical species that can be either oxidized at the anode or reduced at the cathode. In certain embodiments, none of these species or the product produced by oxidation or reduction at the electrodes exists as a gas in the electrolyte, resulting in pumps with highly accurate delivery rates. In the methods of the invention, the electrochemical cell is operated so that the dominant cell reactions are the reactions of the redox couples at the electrodes. When a potential difference is applied between the cell electrodes causing passage of electric current through the electrodes, ions and optionally solvent are transported across the separator. The separator may be ion-selective.

The electrochemical pump may be configured so that passage of current through the cell results in an increase in the pressure of the electrolyte solution or ionic liquid in at least one compartment of the electrochemical cell. Alternatively, the passage of current through the cell in the opposite direction can be used to create a decrease in pressure in at least one compartment within the cell, resulting in suction. Several mechanisms can lead to the change in pressure in one compartment, including asymmetric solvent and/or ion transport through the separator, asymmetric changes in the density of the electrolyte solutions or ionic liquids caused by changes in apparent molar volume during the redox reaction, asymmetric changes in the density of the electrolyte solutions or ionic liquids caused by changes in apparent molar volume upon ion migration between compartments, and combinations thereof. In certain embodiments, the methods and devices of the invention are capable of producing a liquid pressure in at least one compartment of an electrochemical cell of 2 atmospheres or greater. A buildup of fluid pressure in an electrochemical cell compartment can drive flow or spraying of electrolyte solution or ionic liquid from that compartment or be transferred hydraulically to another compartment.

In an embodiment, the invention provides an electrochemical pump comprising an electrochemical cell, the electrochemical cell comprising a first compartment comprising a first electrode and a first electrolyte solution, the first electrolyte solution comprising a first redox couple which participates in a first electrode reaction and may include a first group of ions different from the first redox couple species, wherein neither of the species of the first redox couple is a gas; a second compartment comprising a second electrode and a second electrolyte solution, the second electrolyte solution comprising a second redox couple which participates in a second electrode reaction and may include a second set of ions different from the second redox couple species, wherein neither of the species of the second redox couple is a gas; and an ion conducting separator separating the first and second compartment, the separator being in fluid communication with the first and second electrolyte solution, and wherein the separator may allow transport of at least some species of the first and second groups of ions but restrict transport of the ions of the first and second redox couples.

In another embodiment, the invention provides a selectively controllable valve comprising an electrochemical cell, the electrochemical cell comprising a first compartment comprising a first electrode and a first electrolyte solution, the first electrolyte solution comprising a first redox couple which participates in a first electrode reaction; a second compartment comprising a second electrode and a second electrolyte solution, the second electrolyte solution comprising a second redox couple which participates in a second electrode reaction; and an ion conducting separator separating the first and second compartment; a fluid pathway adjacent to the electrochemical cell; and a flexible diaphragm in fluid communication with one of the first and second electrolyte solutions, wherein expansion of the flexible diaphragm in response to at least one of the first and second electrode reactions at least partially blocks the fluid pathway.

In another embodiment, the electrochemical cell may be configured so that passage of current through the cell results in a change in the volume of electrolyte solution or ionic liquid associated with at least one compartment of the cell. The same mechanisms that can lead to an increase or decrease in pressure can lead to an increase or decrease in volume of electrolyte solution or ionic liquid if the cell is configured to allow flow of fluid out of the compartment, or if the compartment is not completely filled with electrolyte solution or ionic liquid, or expansion of the compartment.

Furthermore, the electrochemical cell may also be configured so that passage of current through the cell results in an increase in both the volume and pressure of the electrolyte solution or ionic liquid associated with at least one compartment of the electrochemical cell.

Changes in the pressure and/or volume of electrolyte solution or ionic liquid associated with one compartment of the electrochemical cell may be used to induce flow of an external fluid (a fluid other than the cell electrolytes or ionic liquids) in a flow channel external to the electrochemical cell. In one embodiment, changes in pressure and volume in one compartment of the cell can be used to drive movement of a flexible diaphragm which forms part of the cell compartment wall. The flexible diaphragm is in hydraulic communication with the fluid in a flow channel so that movement of the diaphragm induces movement of the external fluid in the flow channel.

In another embodiment, the invention provides a microfluidic chip, comprising a first pumping fluid reservoir comprising a first electrode and a first electrolyte solution, the first electrolyte solution comprising a first redox couple which participates in a first electrode reaction and may include a first group of ions different from the first redox couple species, wherein neither of the species of the first redox couple is a gas; a second pumping fluid reservoir comprising a second electrode and a second electrolyte solution, the second electrolyte solution comprising a second redox couple which participates in a second electrode reaction and may include a second set of ions different from the second redox couple species, wherein neither of the species of the second redox couple is a gas; an ion exchange membrane separating the first and second pumping fluid reservoirs, the membrane being in fluid communication with the first and second electrolyte solution, and wherein the membrane may allow transport of at least some species of the first and second groups of ions but restrict transport of the ions of the first and second redox couples; a barrier in communication with the second pumping fluid reservoir; a pumping chamber adjacent the barrier and comprising a volume, the pumping chamber positioned such that expansion of the barrier decreases the volume of the pumping chamber; and a microfluidic channel connected to the pumping chamber, whereby expansion of the barrier causes a solvent within the pumping chamber to flow through the microfluidic channel.

In another embodiment, increases in fluid volume and/or pressure associated with one compartment of the cell cause outward flow of electrolyte solution or ionic liquid through an outlet in that compartment. Outward flow of electrolyte solution or ionic liquid can be used to drive flow of an external fluid in the flow channel away from the compartment. The outlet is in fluid communication with the flow channel containing the external fluid. The electrolyte solution or ionic liquid may be in direct contact with the external liquid in the flow channel or may be separated from the liquid by a hydraulic force transmission element. In an embodiment, the hydraulic force transmission element is located within the flow channel and movement of the hydraulic force transmission element in the flow channel induces flow of the fluid. The hydraulic force transmission element may be gas, liquid, or solid. Similarly, decreases in fluid volume and/or pressure associated with one compartment of the cell can be used to drive flow of an external fluid in a flow channel towards the compartment.

In addition, increases in the pressure and volume of electrolyte solution or ionic liquid associated with one compartment of the electrochemical cell may be used to pressurize a fluid external to the electrochemical cell. In an embodiment, the external fluid is in a closed compartment and a hydraulic force transmission element is located in between the electrolyte solution or ionic liquid and the external fluid.

Furthermore, changes in the pressure and/or volume of electrolyte solution or ionic liquid associated with one compartment of the electrochemical cell can be used to induce movement of a solid body external to the electrochemical cell. In one embodiment, changes in pressure and volume in one compartment of the cell can be used to drive movement of a flexible diaphragm which forms part of the cell compartment wall. The flexible diaphragm is connected to the solid body so that movement of the diaphragm causes movement of the solid body. The solid body may act as a hydraulic force transmission element which in turn transfers force to a fluid external to the electrochemical cell. In other various embodiments, movement of the flexible diaphragm may be used to implement valves that selectively stop or allow flow through a channel or into or out of a compartment, or to actuate switching valves or other actuation-driven components.

DETAILED DESCRIPTION OF THE PREFERRED EMBODIMENTS

The methods and pumps of the invention employ at least one divided electrochemical cell. As referred to herein, an electrochemical cell comprises two or more electrically conducting phases, each pair of electrically conducting phases being connected by an ionically conducting phase. In a divided cell, the cell is divided into two or more compartments, each containing an ionically conducting phase. In an embodiment, the electrochemical cell comprises first and second compartments divided by an ionically conducting separator. In another embodiment, the electrochemical cell may comprise more than two compartments. The cell may be of any suitable configuration or material known to the art to achieve the desired electrochemical configuration and activity of the cell. The cell may be completely rigid, partially flexible, or wholly flexible. The flexibility of the cell is selected depending on the desired mode of operation of the cell. For example, pressure can build up more rapidly in one compartment of the cell if that compartment is rigid. In another embodiment, one or more compartments are flexible, allowing expansion of the compartment.

In a preferred embodiment, a source of electric current or electrical potential is connected between the electrically conducting phases of the cell. Sources of electric current and electrical potential, such as current and power supplies, are known to those skilled in the art. In other preferred embodiments, however, no external source of electrical current or electrical potential is required for operation of the cell.

As used herein, the configuration of an electrochemical cell includes the physical arrangement of the cell, the particular electrolyte solution(s) or ionic liquid(s), and the particular ionically conducting separator(s). The physical arrangement of the cell includes the number of cell compartments and whether individual cell compartments contain outlets or other features such as flexible diaphragms. The configuration of the electrochemical pump includes the electrochemical cell configuration.

In an embodiment, the electrochemical cell can be adapted or configured so that the transfer of ions and optionally solvent across the separator results in a change in the pressure in the electrolyte solution or ionic liquid in at least one of the cell compartments. In certain preferred embodiments, the pressure in the cell is less than about 1 atmosphere, greater than about 1 atmosphere, between about 1 atmosphere and about 10 atmospheres, greater than about 10 atmospheres, or greater than about 20 atmospheres.

Figure 1:
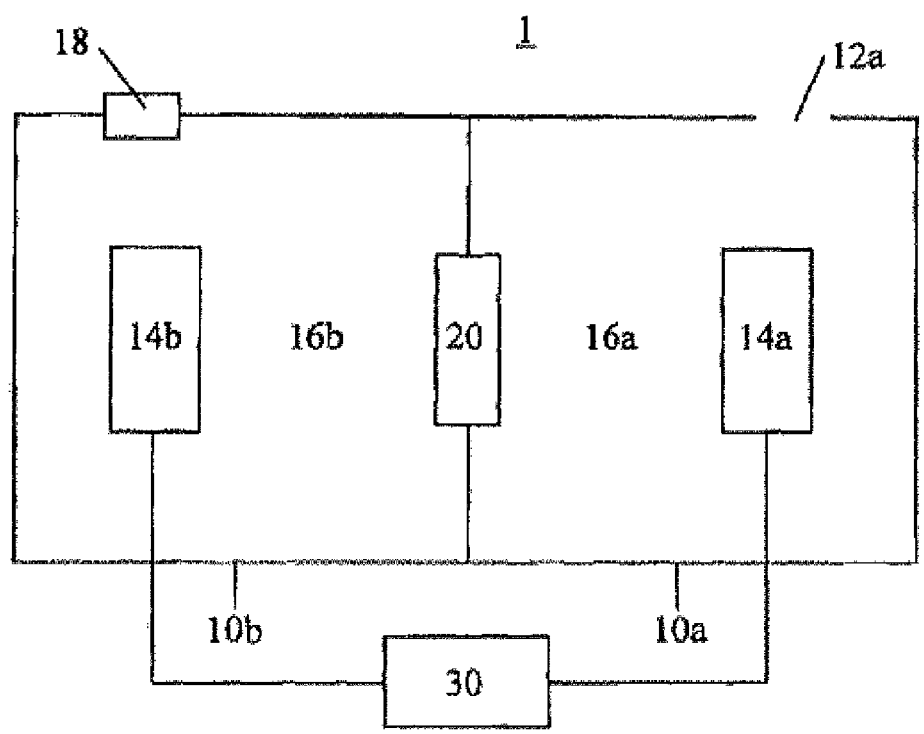
FIG. 1 is a schematic showing an electrochemical pump which produces an increase in pressure in one compartment of the electrochemical cell.

FIG. 1 schematically illustrates a divided electrochemical cell 1 having two compartments 10a and 10b, which is configured to allow pressurization of compartment 10b. Compartments 10a and 10b are separated by ionically conducting separator 20. Compartment 10a may be open to the atmosphere through outlet 12a and contains electrode 14a and electrolyte solution or ionic liquid 16a. Compartment 10b is closed, fitted with a pressure transducer 18 and contains electrode 14b and electrolyte solution or ionic liquid 16b. The two electrodes 14a and 14b are connected through current source 30. The circuit is completed by ionic conduction through liquids 16a and 16b and ionically conducting separator 20. Flow of electrons from electrode 14a to electrode 14b is accompanied by a corresponding flow of positive ions from compartment 10a to compartment 10b. If liquid 16a is an electrolyte solution, there may also be a flow of solvent from compartment 10a to compartment 10b. Electrolyte solutions or ionic liquids 16a and 16b are selected so that transfer of positive ions (and optionally solvent) from compartment 10a to compartment 10b results in an increase in the fluid pressure in compartment 10b.

The change in the fluid pressure in compartment 10b will depend upon the pressure change associated with the redox reaction in this compartment, as well as the pressure changes associated with ion and solvent transfer across the separator. If the pressure change associated with the redox reaction itself is small, the overall pressure change associated with the cell reaction will be dominated by ion and solvent transfer across the separator. In an embodiment, at least one ion species having a large apparent molar volume is transported across the separator from compartment 10a to compartment 10b.

Figure 2:
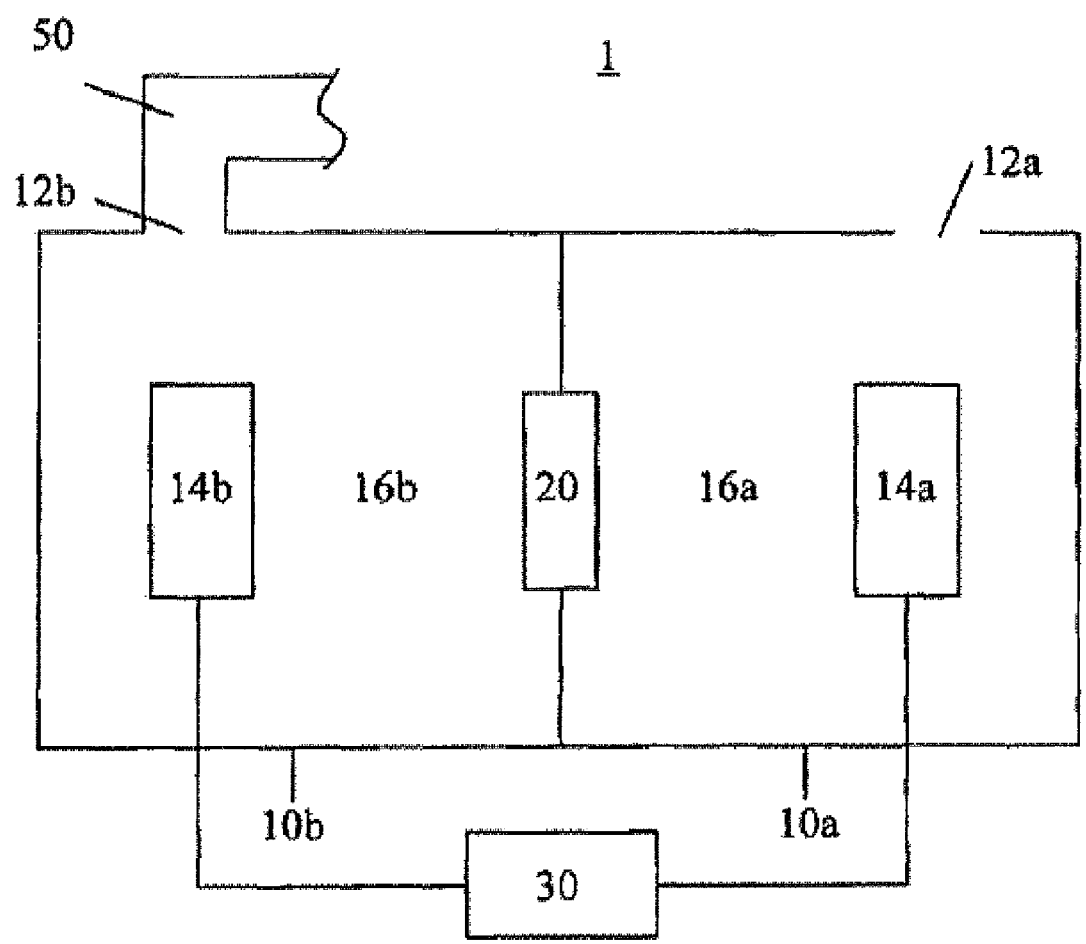
FIG. 2 is a schematic showing an electrochemical pump which produces electrolyte solution or ionic liquid flow out of one compartment of an electrochemical cell.

In another embodiment, the electrochemical cell is configured so that the transfer of ions and optionally solvent across the separator results in an increase in the volume of electrolyte solution or ionic liquid on one side of the separator and associated with one of the cell compartments. An increase in volume of electrolyte solution or ionic liquid causes flow of electrolyte solution or ionic liquid out of the compartment if the cell compartment is filled with electrolyte solution or ionic liquid and the volume of the cell compartment is fixed. FIG. 2 schematically illustrates a divided electrochemical cell 1 having two compartments 10a and 10b, which is configured to allow fluid flow in or out of compartment 10b. Compartments 10a and 10b are separated by ion-conducting separator 20. Compartment 10a may be open to the atmosphere through outlet 12a and contains electrode 14a and electrolyte solution or ionic liquid 16a. Compartment 10b is connected to a flow channel 50 through outlet 12b and contains electrode 14b and electrolyte solution or ionic liquid 16b. The two electrodes 14a and 14b are connected through current source 30. The circuit is completed by ionic conduction through liquids 16a and 16b and ionically conducting separator 20. Electrolyte solutions or ionic liquids 16a and 16b are selected so that transfer of positive ions (and optionally solvent) from compartment 10a to compartment 10b results in an increase in the electrolyte solution or ionic liquid volume associated with compartment 10b, which in turn leads to flow of electrolyte solution or ionic liquid out outlet 12b.

The volume change associated with compartment 10b can also depend upon the apparent molar volume change associated with the redox reaction, as well as the apparent molar volume change due to ion and solvent transfer across the separator. The volume of electrolyte solution or ionic liquid is referred to as the volume associated with the cell compartment rather than the volume in the cell compartment because the volume of electrolyte solution or ionic liquid associated with a compartment can be greater than the compartment volume and therefore may not be confined to that compartment. For example, if that compartment is filled with fluid, the change in volume may manifest itself as an outward flow of fluid from that compartment. If the apparent molar volume change associated with the redox reaction itself is small, the overall volume change associated with the cell reaction will be dominated by ion transfer and optionally solvent transfer across the separator.

The present invention can also be used to drive flow of a fluid in an external flow channel, the fluid being other than the electrolyte solution or the ionic liquid in the compartment driving the flow. In another embodiment, the cell compartment further comprises a flexible diaphragm and the cell compartment is filled with electrolyte solution or ionic liquid. In an embodiment, the flexible diaphragm is impermeable to the ionic solution or liquid. In another embodiment, the diaphragm is semipermeable to the ionic solution or liquid. When the flexible diaphragm contacts fluid in a flow channel external to the electrochemical cell, the increase in fluid volume and pressure associated with the compartment causes deformation of the diaphragm, which in turn can be used to induce flow of fluid in a flow channel external to the electrochemical cell. The flow channel may or may not be directly connected to the electrochemical cell. Any suitable material known to the art may be used for the diaphragm, including polymeric materials and sufficiently thin sections of non-polymeric materials such as silicon, glass and metal. The diaphragm material is selected to be chemically compatible with the electrolyte solution or ionic liquid as well as the fluid in the flow channel.

In another embodiment, the flow channel is in fluid communication with an outlet in one of the compartments of the electrochemical cell. As shown schematically in FIG. 2, the flow channel may be connected directly to the compartment wall. A hydraulic force transmission element may be present in the flow channel, located between the electrolyte solution or ionic liquid from the cell compartment and the fluid to be pumped in the flow channel. The hydraulic force transmission element is used to separate the electrolyte solution or ionic liquid from the fluid to be pumped and also to transfer hydraulic force from the electrolyte solution or ionic liquid to the fluid to be pumped. In an embodiment, the hydraulic force transmission element may be a gas, such as a bubble. In another embodiment, the hydraulic force transmission element may be a liquid. The liquid acting as the hydraulic force transmission element may be selected so that mixing is limited between the hydraulic force transmission liquid and both the fluid to be pumped in the flow channel and the electrolyte solution or ionic liquid. In an embodiment, the liquid hydraulic force transmission element is selected so that it is immiscible with and does not react with the fluid(s) to be moved through the device. The liquid hydraulic force transmission element can be preferably selected so that it wets the flow channel with equal or greater wettability than the fluid(s) to be moved through the device. These miscibility and wetting conditions allow formation of a "slug" of liquid between the electrolyte solution or ionic liquid and the fluid in the flow channel. The viscosity of the liquid hydraulic force transmission element is preferably selected so that its resistance to flow can be overcome by the flow of electrolyte solution or ionic liquid from the electrochemical cell. In another embodiment, the hydraulic force transmission element is a solid.

In another embodiment, the electrochemical cell is adapted or configured so that the transfer of ions and optionally solvent across the separator results in both an increase in the pressure in the electrolyte solution or ionic liquid in one of the cell compartments and an increase in the fluid volume associated with that compartment. If the compartment is filled with electrolyte solution or ionic liquid, the pressure in the compartment increases if the mechanisms leading to an increase in pressure are not counterbalanced by flow of electrolyte solution or ionic liquid out of the compartment or by some other mechanism (e.g. expansion of the compartment). In an embodiment, the cell compartment is filled with electrolyte solution or ionic liquid and the volume of the cell compartment is fixed. The increase in fluid volume associated with the compartment causes flow of electrolyte or ionic liquid out of the compartment. Flow through the outlet is sufficiently restricted that the pressure in the cell compartment increases. The pressure change in the compartment will depend on the flow rate of electrolyte solution or ionic liquid out of the cell, as well as the pressure changes associated with the redox reaction and ion and solvent transfer across the separator.

In one embodiment, the current through the electrochemical cell depends on the magnitude and polarity of the applied potential. In various embodiments, the current density may be less than 1 $\mu A/cm^2$, or between about 1 $\mu A/cm^2$ and 1 $mA/cm^2$, or between about 1 and about 1500 $mA/cm^2$, where the current density is based on the separator cross-sectional area and other factors. For example, where a Nafion® (a sulfonated perfluoropolyethylene sold by DuPont) ionically conducting membrane is employed, which is generally considered to have an effective or equivalent pore diameter of about 4 nm, a preferred current density would be up to about 500 $mA/cm^2$. Preferably, the cell current is less than the mass-transport limited current associated with oxidation or reduction of the redox couple. These current densities can be achieved with applied potentials less than about 10 V for pumps of relatively small size, although larger pumps may require higher applied potentials. In an embodiment using a small pump and a Nafion® ionically conducting membrane, the applied potential is preferably less than about 1 V.

As used herein, an electrolyte solution is a solution containing an electrolyte. Electrolytes include ionic liquids and chemical compounds that dissociate into electrically charged ions when dissolved in a solvent. The solvent is often selected so that the electrolyte is soluble and stable in the chosen solvent. The electrolyte solution in adjacent compartments of the cell may be the same or different. In an embodiment, each compartment of the electrochemical cell contains an electrolyte solution, with the solvent being the same in each compartment. The solvent and redox concentrations may be the same in each compartment, or may be different. In another embodiment, each compartment contains the same ionic liquid. In an embodiment, at least one compartment contains an electrolyte solution and at least one compartment contains an ionic liquid.

In the present invention, the electrolyte solution or ionic liquid present in each compartment comprises a redox couple.

As used herein, a redox couple is a pair of chemical species linked by a given half reaction (either oxidation or reduction) at an electrode. The redox species may or may not be transported across the separator. In addition, some of the redox species may be transported while others are not. The electrolyte or ionic liquid may consist essentially of the redox couple or may comprise additional ionic species. The additional ionic species may also be transported across the separator. The redox couple in adjacent compartments may be the same or different.

An "active" redox couple is selected so that under the conditions of operation of the cell the predominant electrode reaction is either oxidation or reduction of the active redox couple. Determination of whether a particular redox couple will be active under given cell operation conditions is known to those skilled in the art. The electrolyte solution or ionic liquid may further comprise an additive chelating agent or complexing agent to shift the standard electrode potential of the redox reaction. The redox couple may be inorganic, organometallic, or organic. Inorganic redox couples include, but are not limited to, iodide/iodine. Organometallic redox couples include, but are not limited to ferricyanide/ferrocyanide. Organic redox couples include, but are not limited to quinone/hydroquinone. In an embodiment, both redox species are ions. In another embodiment, both redox species are anions. In another embodiment, at least one of the redox species is neutral.

The redox couple is preferably selected so that neither of the species in a particular redox couple is gaseous under the cell operating conditions. In an embodiment, the current efficiency for any electrode reaction that produces a gas is less than about one percent.

Each electrolyte solution or ionic liquid present in a compartment may further comprise an additive which provides additional ions which are different from the redox couple species in that compartment. In an embodiment, at least some of these additional ions are transported across the ionically conducting separator. Such an additive may be used when the redox couple species are not transported across the separator, but may also be used when the redox couple species are transported across the separator. Useful additive ion species include, but are not limited to, alkylammonium ions, including tetraalkylammonium ions such as tetrapropylammonium (TPA+) and tetrabutylammonium (TBA$^+$), alkali metal ions such as Li$^+$, Na$^+$, K$^+$, and TRISH$^+$ (tris(hydroxymethyl)aminomethaneH$^+$). In an embodiment, one or more of the ion species listed above is used in combination with a sulfonated perfluoropolyethylene cation exchange membrane such as Nafion®.

In one embodiment, the redox couples and optional electrolyte or ionic liquid additives are selected in combination with the ionically conducting separator to obtain the desired relationship between the current through the electrochemical cell and the flow rate and/or change in fluid pressure. The overall change in fluid volume or pressure in a cell compartment depends on the combined effect of the volume change associated with the overall chemical change occurring in the compartment (the overall chemical change being a combination of the redox reaction and ion migration) and, if applicable, the volume change associated with solvent migration.

The redox reaction may be selected to provide a small change in apparent molar volume. For example, for the redox reaction $I_3^{31}$ +2 e$^-$ →3I$^-$, the apparent molar volume of $I_3^-$ has been shown to be close to that of 3 I$^-$ in some solutions (Norman et al., 2004, J. Electrochem. Soc., 151(12), E364-D371; Norman et al., 2005, Anal. Chem., 77(10), 6374-6380). In one embodiment, when an increase in fluid pressure or volume is to be obtained in a particular cell compartment, the redox reaction in that compartment is selected so that it does not produce an apparent molar volume decrease upon reduction.

In one embodiment, the species being transported across the separator may also be selected to have a relatively large apparent molar volume. The ion species is selected to be small enough to allow sufficient transport of the ion species across the separator. In a preferred embodiment, the apparent molar volume of at least one ion species being transported across the separator is at least about 10 $cm^3$/mol. In other embodiments, the apparent molar volume is at least about 25 $cm^3$/mol, at least about 50 $cm^3$/mol, or at least about 100 $cm^3$/mol.

Suitable electrolyte solvents for use with the present invention are those which allow solvation of the selected redox couples and electrolyte additives. In an embodiment, the solvents allow the concentration of the redox couple or electrolyte additive in solution to be greater than about 0.1 mol/L. These electrolyte solvents include, but are not limited to, water, dimethylformamide (DMF), aqueous organic ether mixtures, aqueous acetonitrile, ionic liquids and task specific ionic liquids for which the redox couple is part of the ionic liquid.

As used herein, an ionic liquid is a liquid consisting only of anions and cations. Suitable ionic liquids for use with the present invention include, but are not limited to room temperature ionic liquids, such as 1-butyl-3-methylimidizolium tetrafluoroborate.

In an embodiment, the open circuit voltage of the electrochemical cell is zero. As used herein, the open circuit voltage of the electrochemical cell is the voltage of the cell under zero current conditions. An open circuit voltage of zero can be achieved by using the same electrolyte solution or ionic liquid in all compartments of the cell. In another embodiment, the open circuit voltage of the electrochemical cell is nonzero.

In one embodiment, an inert electrode is used that does not take part in any reactions under the conditions of the oxidation/reduction of the redox forms. Suitable electrodes for the practice of the invention include graphite and inert metals such as platinum. In an embodiment, the electrodes are in a form which provides a high surface area. An electrode may also take part in the redox reaction, for example Ag/AgCl. The electrode material in adjacent cell compartments may be the same or may be different.

The electrochemical cell compartments are separated by an ionically conducting separator. At least a portion of the ionically conducting separator is ionically conducting. The ionically conducting portion of the separator can be a solid or a liquid. In an embodiment, the ionically conducting portion of the separator is a membrane. In an embodiment, membranes suitable for use with the present invention form an integral layer and so do not include non-cohesive packed particles unless the effective or equivalent pore diameter is less than about 100 nm. For applications in which development of significant pressures (greater than about 1 bar) is desirable, membranes with relatively low hydraulic permeability are used. Useful membranes with sufficiently low hydraulic permeability can have pores less than about 100 nm in diameter. In various preferred embodiments, ionically conducting membranes may have effective or equivalent pore sizes less than 50 nm in diameter, and as small as about 1 nm in diameter. Suitable ionically conducting membrane materials are well known in the art and include hydrocarbon ion exchange membranes (for example, RALEX® from Mega a.s. and Selemion® from ACG Engineering, Nafion® (a sulfonated perfluoropolyethylene sold by DuPont) and other fluorocarbon ion exchange membranes (for example, Flemion® sold by Asahi Glass Co.). In an embodiment, the ionically conducting membrane is an ion exchange membrane. Ion exchange membranes may be homogeneous or heterogeneous. In an embodiment, the ionically conducting membrane is a heterogeneous ion exchange resin pressed into a flexible backing, such as Ionac® (Sybron Chemicals, Inc.) and Ultrex™ (Membranes International, Inc.). In an embodiment, the membrane is a cation exchange membrane. Ionically conducting glasses are also suitable for the practice of the invention. In an embodiment, the membrane is selected to allow asymmetric solvent transport or an asymmetric change in the density of the electrolyte solutions or ionic liquids when current passes through the cell. Preferably, the membrane is sufficiently chemically compatible with the ionic solution(s) or liquid(s) that any degradation of the membrane by the fluids does not substantially affect transport through the membrane during the time period of interest.

In one embodiment, the ionically conducting separator is selected to allow a sufficient electrically-driven flux of the desired ion species through the separator. The separator may be permselective, so that the flux of different ion species through the separator differs. In one embodiment where ions different from the redox species are added to the electrolyte, the separator may be used to allow transport of at least some of the non-redox ion species but restrict transport of the redox species. In an embodiment, the flux of the redox species is restricted to be less than about 1%. Use of an ion exchange membrane allows selection of the sign of the charge of the ions which will be transported across the membrane. For example, the cell may comprise electrolyte solutions with anionic redox couples and electrolyte additives which provide cations having a relatively large apparent molar volume. If a cation exchange membrane is used in the cell, the cations are the ions which will be transported across the membrane.

When it is desired to transport solvent across the ion permeable separator, the separator is selected to have a sufficiently high transference coefficient to produce the desired solvent flow rate across the separator. In different embodiments, the transference coefficient is at least about 3.5, at least about 4, or at least about 5.0. For at least some ion exchange membranes, the transference coefficient of a membrane for a particular ion/solvent combination correlates with the degree of solvent swelling of the membrane when the ions are present in the membrane. Okada et al. have shown that for Nafion® membranes, alkali metal ions which attract more water molecules in the membrane, which was reflected as increased solvent swelling, transported more solvent molecules (Okada, T. et al., 2002, J. Phys. Chem. B., 106, 1267).

To increase the pressure of the ionic liquid or electrolyte solution in one of the compartments, the increase in fluid pressure due to the combination of forward flow of ions and optionally solvent across the separator and the changes in apparent molar volume for the redox reaction needs to be greater than the decrease in pressure due to back flow of solvent (and due to the decrease in pressure due to flow out any outlets or due to compartment expansion). The rate of backflow of solvent through the membrane depends upon its hydraulic permeability. Therefore, the hydraulic permeability of the membrane is another factor in membrane selection when pressurization of the ionic liquid or electrolyte solution is desired.

For pressurization of the electrolyte solution or ionic liquid in a rigid compartment, the energy conversion efficiency can be estimated as $$\text{energy conversion efficiency} = (V \Delta P)/IEt \qquad \text{Equation 1}$$

where V is the compartment volume, ΔP is the increase in pressure, I is the current, E is the potential and t is the time (if it can be assumed that there is no liquid flow out from the pressurized compartment). Mechanisms contributing to loss of efficiency include mechanical membrane deformation, backflow through the membrane, and Joule heating effects. In an embodiment, the efficiency is greater than about 2%.

A support structure may be used to hold the ionically conducting separator and optionally reduce its deflection under pressure. The support structure is configured specifically for each type of ion conducting separator and allows contact between the electrolyte solution(s) and the separator. In an embodiment, the support structure has an array of holes, the holes being approximately ⅛" (3.2 mm) in diameter. In another embodiment, further support is provided by a mesh structure sandwiched between the array of holes support and the ion conducting separator when the separator is a membrane. Such a mesh structure adds further support to minimize deflection of the ion conducting membrane. An example of the mesh support is nylon mesh filters with pore diameters of 100 micrometer (Millipore, NY1H). Support materials may be made of any suitable material know to those skilled in the art which is chemically compatible with the ionic solution(s) or electrolyte solution(s).

Figure 3A:
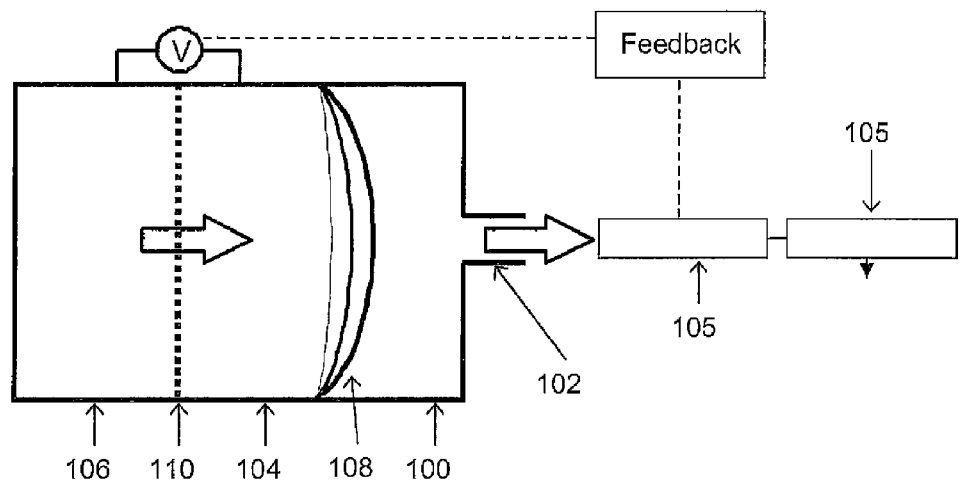
FIG. 3A is a diagram illustrating a pump according to a preferred embodiment of the present invention.
Figure 3B:
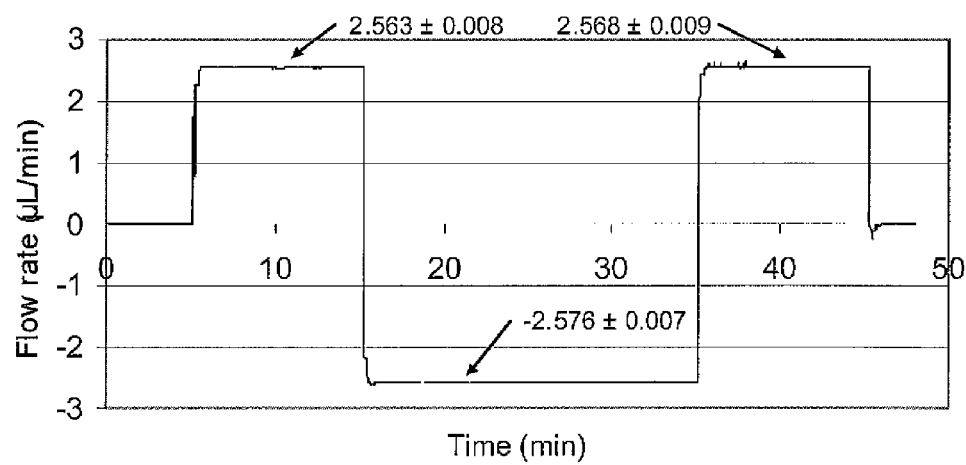
FIG. 3B is a graph illustrating the experimental results from one particular implementation of the pump design of FIG. 3A.

One preferred embodiment of the present invention for a "single-ended" pump configuration is illustrated in FIG. 3A. In this three-layer configuration, pumping fluid moves from the left reservoir 106 through ion conducting separator 110 to the right reservoir 104, thereby pushing on flexible diaphragm 108, which in turn forces liquid (or gas) from pumping chamber 100 into channel 102. The liquid in the pumping chamber may be solvent or buffer, or may be air that then pushes solvent/buffer already present in channel 102. The solvent/buffer passing through channel 102 may preferably be directed through two independent flow sensors 105 connected by tubing. The first flow sensor 105 provides feedback to the voltage supply, making small adjustments in the applied voltage to keep the flow rate constant. The second flow sensor 105 provides output of the measured flow rate to an output device. Alternatively, flow measurement and feedback functions can be provided by a single flow sensor. In this manner the flow rate can be programmed to deliver fluid (positive flow) or withdraw fluid (negative flow). The results of pumping at 2.5 microliters/minute in a particular embodiment as shown in FIG. 3A—first forward, then reverse, then forward—is illustrated by the graph of FIG. 3B. The average and standard deviation of the measured flow rate is given for each flow direction. The accuracy and precision of the measured flow rate is within the specifications provided for the flow sensor, indicating that the flow sensor, not the pump, may be limiting the accuracy and precision of fluid flow.

It may be seen that the device shown in FIG. 3A may be utilized in a number of ways. It may be used as a simple pump, that is, to move liquid/gas directly via flexible diaphragm 108; without flexible diaphragm 108 with direct contact between the pumping fluid and the pumped fluid; with a gas bubble or immiscible plug separating the fluids; operated with or without feedback control; operated as an oscillating pump with a check valve; or operated with two check valves and a refill reservoir. Other pump configurations are possible. The pump may also be used as a switchable valve, such as by using pressure to force a solid block into and out of a channel or to pressurize a diaphragm to block or open a flow channel.

Figure 4:
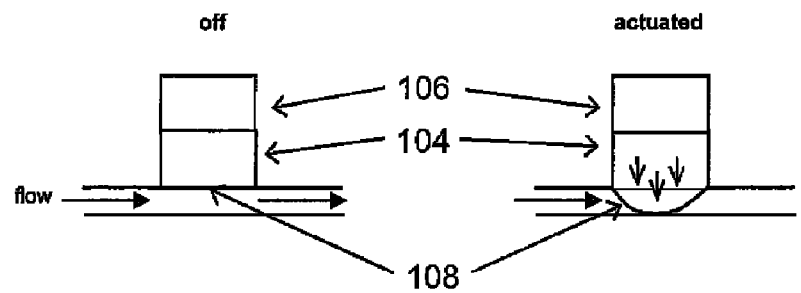
FIG. 4 is a diagram illustrating a valve according to a preferred embodiment of the present invention.

A particular application of the pump used to implement a "pinch" valve function is shown in FIG. 4. Pumping fluid moves from upper reservoir 106 to lower reservoir 104, thereby pushing on flexible diaphragm 108, the expansion of which closes off the flow through the channel shown. Although the closing of a flow path is illustrated, the device could alternatively be used to close off or open the entrance to a fluid/gas chamber. Single or multiple valves could be accessed using a single pump. Dual operation is also possible in various embodiments, where one end of a pump in such a device could close a valve, while the other end simultaneously opens another valve. The pump may also be used to perform mixing operations; since forward and reverse flow operations are possible by simply switching the direction of applied potential, mixing may be performed by oscillating the flow direction with materials to be mixed in pumping chamber 100.

Stroke volume may be defined as the ability of a device to continuously deliver in one direction without any interruption. It will be seen that in those embodiments of the present invention directed to a single-sided pump, such as illustrated in FIG. 3A, the stroke volume is limited by the amount of redox material available for reaction. This is limited by electrode design and the solubility of the redox couple in the pumping solution. To the extent that more redox material may be made available, however, stroke volume may be increased. Therefore, in various embodiments of the present invention, stroke volume may thus be increased by a number of methods. In one series of embodiments, stroke volume may be increased by using a solid that goes into/out of solution in the pumping solution. For example, solubility is a function of temperature for certain solids, and thus by varying the temperature of the pumping solution the solubility of the solids may be raised or lowered. In one embodiment, Peltier heating units may be used to control temperature at the pump, and thereby control the solubility of solids used for this purpose. For example, even the small temperature change from 25° C. to 35° C. results in a 10% increase in the molar solubility of iodine in a 1 M aqueous potassium iodide solution (R. W. Ramette and R. W. Sandford, Jr., Thermodynamics of Iodine Solubility and Triiodide Ion Formation in Water and in Deuterium Oxide, *J. Am. Chem. Soc.*, 1965, 87 (22), 5001-5005).

Another method for controlling solubility is the encapsulation of redox components. Inclusion complexes that trap and then release redox components may be employed in certain embodiments of the present invention. Although the addition of a chelating agent or complexing agent has been discussed above for the purpose of shifting the standard electrode potential of the redox reaction, such agents may be added for the purpose of controlling solubility. In still other embodiments, a series of coupled redox reactions may be employed in the pumping fluid for the purpose of raising stroke volume. For example, a first redox reaction may create a species that is redox active at a higher potential, so the pump first operates at a lower potential, then the potential is raised when the reaction begins to slow so that pumping continues. Vanadium, for example, is a material with four stable ionic states plus a neutral state, and which has been successfully employed in batteries using sulfuric acid electrolytes. Certain embodiments of the present invention may thus utilize Vanadium in conjunction with varying applied potentials to increase stroke volume.

Figure 5:
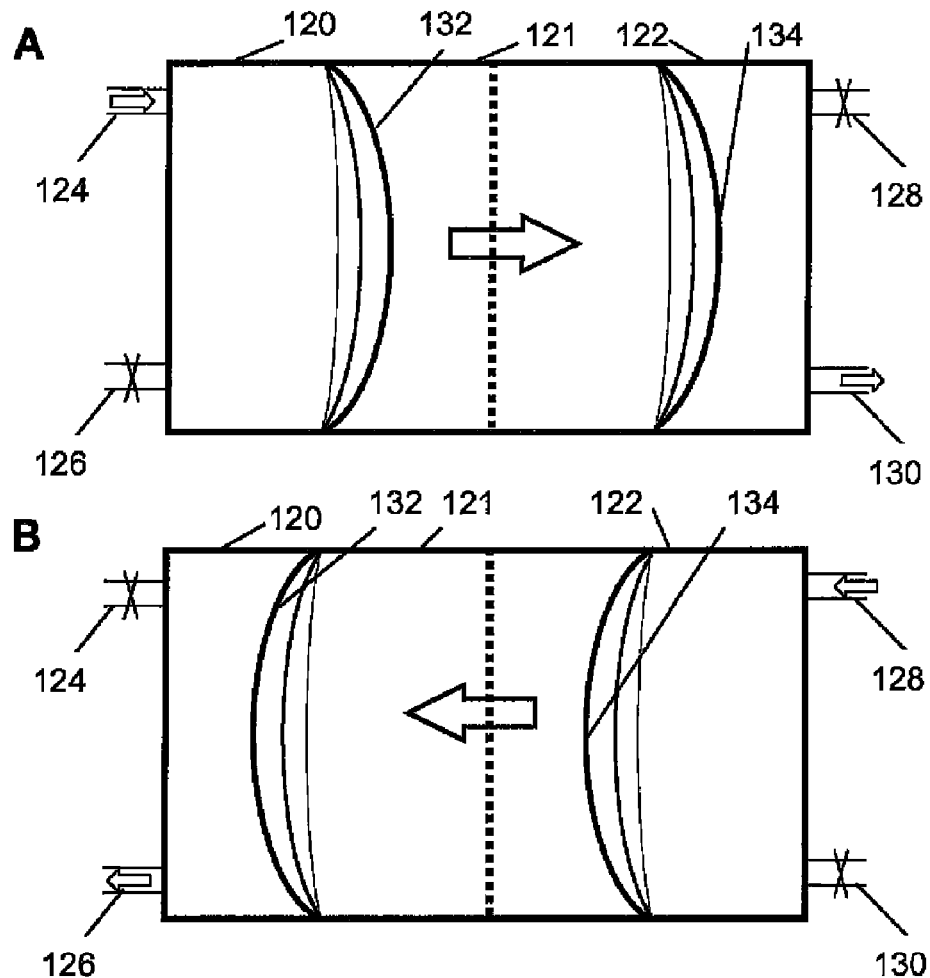
FIG. 5 is a diagram illustrating a continuous flow pump implemented with a two-sided microfluidic pump according to a preferred embodiment of the present invention.

Yet another application of the present invention in various embodiments includes pump configurations allowing for continuous, uninterrupted operation. Existing syringe pumps are inherently limited in that once the volume of the syringe has been emptied, no further pumping is possible without reloading of the syringe. A continuous flow pump may be configured according to one embodiment of the invention using a dual-sided pump mechanism in a "push-pull" arrangement, as shown in FIG. 5. The stroke volume of this embodiment of the invention is effectively infinite, being limited only by the available fluid in an external reservoir. It may be seen that one side of the pump is delivering liquid/gas while the other end is refilling, and then the roles are reversed. As shown in FIG. 5, at time "A" solvent is delivered from a supply container (not shown) to left compartment 120 by means of inlet 124. Solvent in right compartment 122 leaves the pump to the experiment or application of interest by means of outlet 130. Outlet 126 and inlet 128 are effectively closed by means of a one-way check valve or other valve, as are well known in the art. Activation of the pump as shown at time "A" causes the rightward expansion of left half diaphragm 132, and consequently the expansion of right half diaphragm 134 due to the exertion of force within center compartment 121. The result is that solvent is drawn into the pump through inlet 124 and pushed out of the pump at outlet 130. After some time limited only by the maximum single-direction stroke volume, voltage/current driving the pump is reversed, resulting in the configuration shown at time "B." Here, solvent is drawn into the pump through inlet 128 and thereby into right compartment 122, and pushed out to the experiment or application of interest at outlet 126 from left compartment 120. One-way check valves or other valves known in the art prevent the flow of solvent in the wrong direction at inlet 124 and outlet 130. Leftward expansion of diaphragms 132 and 134 causes the flow of solvent as described. The voltage/current may be continually reversed in sequence repeating these steps, for a continuous flow of solution by means of the pump.

Figure 6:
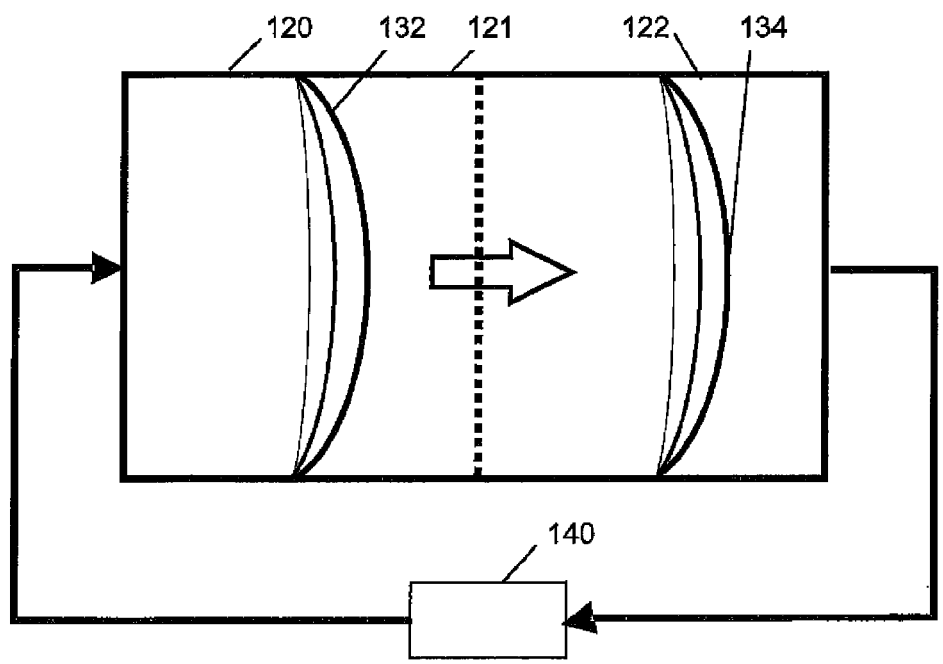
FIG. 6 is a diagram illustrating a continuous flow pump implemented with a two-sided microfluidic pump where a constant volume of solvent liquid is required for the application according to a preferred embodiment of the present invention.

FIG. 6 shows an alternative configuration to provide continuous pumping according to another preferred embodiment of the present invention. In this configuration, solvent is added to and removed from application 140 at the same time. Reversal of the pump operation as described with reference to FIG. 5 causes the direction of flow to be repeatedly reversed, but flow is effectively continual. This configuration may be important for closed-system applications where the volume of fluid must remain constant. FIG. 6 illustrates solvent being moved adjacent to left compartment 120 and moving away from right compartment 122 due to the action of the pump as diaphragms 132 and 134 are expanded rightward, but it will be understood that the application of reverse voltage will cause flow of solvent in the opposite direction.

Figure 9:
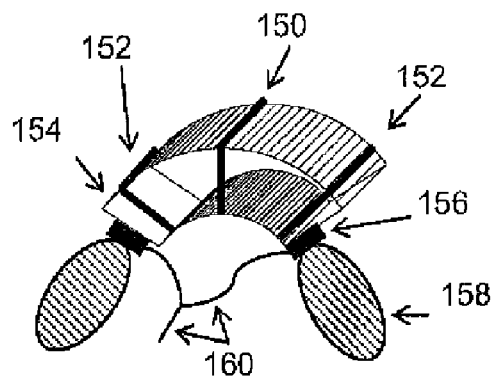
FIG. 9 is a diagram illustrating a "backpack" implementation of a preferred embodiment of the present invention useful for animal applications.

In contrast with mechanical pumps, the various embodiments of the present invention are not inherently limited with regard to shape or geometry. Because mechanical pumps are limited in their possible shapes, this has not heretofore been a common design parameter, but is important in certain applications. For example, the shape and geometry of a pump could be designed to fit into an available space where space is limited, such as a straw-shaped pump that could be "snaked" into a small space for airborne or spaceborne applications where space is at a premium. Other possible applications include human body implantation where a particular shape is desirable, such as for drug delivery to a specific organ/tumor, or external drug delivery devices that could be shaped as earrings, bracelets, or other jewelry. Pumps shaped as "backpacks" that are shaped to fit animals for testing or research purposes are also possible. With respect to this last application, many current pump designs require a research animal to be tethered to a remote pump, which greatly limits the animal's freedom of movement, and may interfere with or complicate testing and research procedures. One embodiment of the dual-sided pump is shown in FIG. 9 where the pump is shaped to fit on the back of an animal (for example, mouse or rat). The pump could be secured to the animal with a jacket or holder. Membrane 150 and diaphragms 152 operate in a manner similar to that already described. Similar to the design in FIG. 5, check valves 156 could be used to fill internal reservoirs 154 from detachable reservoirs 158 for continuous medication delivery to the animal by way of tubing and cannula 160. Detachable reservoirs 158 could be connected to the pump through a self-sealing fluidic connection. Alternatively, medication reservoirs 158 can be integrated directly into the pump and not be detachable. In one embodiment, this pump is about the size of a quarter. In another embodiment, it is about the diameter of a baseball. The pump can be scaled and shaped for different size animals and for implementation externally, subcutaneously, or as an implantable device. Table 1 provides certain examples of various shapes and sizes that may be implemented using various embodiments of the current invention for various applications, although the invention is not limited to the stated shapes and sizes. Maximum pump stroke and maximum flow rate values have been calculated based on expected performance for single-sided pumps. Methods used for estimating the maximum pump stroke and the maximum flow rate values in the following Table are highlighted below. The 'maximum pump stroke' ($V_{maxstroke}$) describes total flow volume produced during the maximum continuous flow in one direction. The maximum pump stroke can be estimated based on the total redox material available during a single stroke. This estimation can be readily accomplished by approximating that 75% of the initial redox concentration will be available for reaction and using Faraday's constant (96485 C/equiv), the compartment volume ($V_{compartment}$), initial concentration of the electrochemical redox couple ($C_{initial}$), and the pumping volume per coulomb ($\Delta V/q$).

$$V_{maxstroke}=(0.75)(96485)(V_{compartment})(C_{init})(\Delta V/q) \quad \text{Equation 2}$$

The pumping volume per unit charge ($\Delta V/q$) is the change in the volume of material per charge. For the case where ion transport across the ion conducting separator is the predominant mechanism, this value is the volume carried across the separator by each charge and is characteristic primarily of the ion conducting separator, the ion being transported, and the solvent. Estimates of the maximum pump stroke shown in the table are based on a specific ion conducting separator (Nafion 117 ion-selective membrane), a 0.25 M concentration of redox aqueous solution, and lithium ion as the mobile ion ($\Delta V/q$=2.8 µL/C). The maximum flow rate shown in the table is estimated based on the maximum current density that can be sustained for the ion conducting separator, $F_{max}$ (i density). For the estimates in this table, the assumption is that the maximum current density that can be sustained through the ion conducting separator provides a good estimate of the maximum flow rate. In this case, the current density limited maximum flow rate, $F_{max}$ (i density), is defined by the pumping volume per charge ($\Delta V/q$), the cross-sectional separator area ($A_{separator}$), and the maximum current density of the separator, $(i/A)_{max}$.

$$F_{max}(i \text{ density})=(\Delta V/q)(A_{mem})((i/A)_{max}) \quad \text{Equation 3}$$

This current-density based calculation may overestimate the maximum flow rate because the maximum redox current (and therefore maximum flow rate) may be further limited by mass transfer to the electrode surface. The actual maximum flow rate will be limited by a number of kinetic parameters and can be more accurately modeled using more complex methods.

Figure 7:
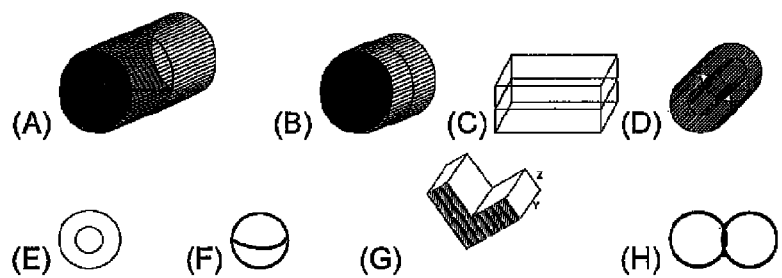
FIG. 7 is an illustration of various possible shapes of pumps according to preferred embodiments of the present invention.

| Shape Class | Shape | Internal dimensions (cm) | Aspect Ratio | Max. pump stroke (μL) | Max. flow rate (μL/min) |
|---|---|---|---|---|---|
| stacked cylindrical (FIG. 7A) | ⅛" × ⅛" | φ 0.32 × h 0.32 | 1:1 | 1 | 7 |
| | column | φ 0.5 × h 0.5 | 1:10 | 25 | 16 |
| | miniature | φ 1.25 × h 1.9 | 1:1.5 | 68 | 103 |
| | 1" × 1" | φ 0.25 × h 0.25 | 1:1 | 300 | 400 |
| | 4" × 4" | φ 10 × h 10 | 1:1 | 20000 | 6600 |
| stacked disks (FIG. 7B) | watch battery | φ 1.0 × h 0.4 | 2.5:1 | 8 | 66 |
| | quarter | φ 2.4 × h 0.165 | 14.5:1 | 19 | 380 |
| | pancake | φ 5.9 × h 0.7 | 8.4:1 | 340 | 2300 |
| stacked rectangular (FIG. 7C) | deck of cards | 8.8 × 6.2 × 1.3 | 6.8:4.8:1 | 1800 | 4600 |
| | die | 1.6 × 1.6 × 1.6 | 1:1:1 | 100 | 210 |
| | credit card | 8.5 × 6.4 0.085 | 100:75:1 | 100 | 3900 |
| | cell phone | 10 × 4.7 × 1.4 | 7.1:3.4:1 | 1800 | 7100 |
| | 1" cube | 2.5 × 2.5 × 2.5 | 1:1:1 | 400 | 520 |
| | sheet of paper | 28 × 21.6 × 0.01 | 2800:2160:1 | 153 | 51000 |
| | 10-sheet thickness | 28 × 21.6 × 0.1 | 280:216:1 | 1530 | 51000 |
| cylinder within cylinder (FIG. 7D) | drinking straw | φ 0.35 × φ 0.5 × 20 | 1:1.4:57 | 100 | 1900 |
| | ⅛" tube | φ 0.23 × φ 0.32 × 100 | 1:1.4:435 | 204 | 6000 |
| sphere within a sphere (FIG. 7E) | golf ball | φ 4.3 × φ 3.4 | 1 | 1000 | 3000 |
| stacked sphere (FIG. 7F) | golf ball | φ 4.3 | 1 | 1000 | 1200 |
| "V" (stroke × depth × width of stroke; FIG. 7G) | small | 1 × 1 × 2.5 | 2:2:1 | 25 | 60 |
| | large | 5 × 5 × 2.5 | 2:2:1 | 3200 | 1500 |
| dumbbell (FIG. 7H) | small | φ 1 × φ 1 × 0.5 | 2:2:1 | 30 | 70 |
| | large | φ 4.3 × φ 4.3 × 3 | 1.4:1.4:1 | 2000 | 600 |

The invention is scalable to almost any size in various embodiments, including the very small sizes that would be needed in order to incorporate the pump onto a microfluidic chip, that is, "pump on a chip" applications. The non-mechanical nature of certain embodiments of the invention means that there are no moving, mechanical parts to limit size for miniaturization. In a three-layer microfluidic chip implementation using the general approach of the pump of FIG. 3A, pumping fluid moves from a lower to upper reservoir through an ion conducting separator, thereby pushing on a flexible diaphragm, which in turn forces liquid (or gas) from the pumping chamber into a microfluidic channel. The liquid in the pumping chamber may be solvent or buffer needed for chip function, or may be air that then pushes the solvent/buffer already present in the microfluidic channel.

Figure 8:
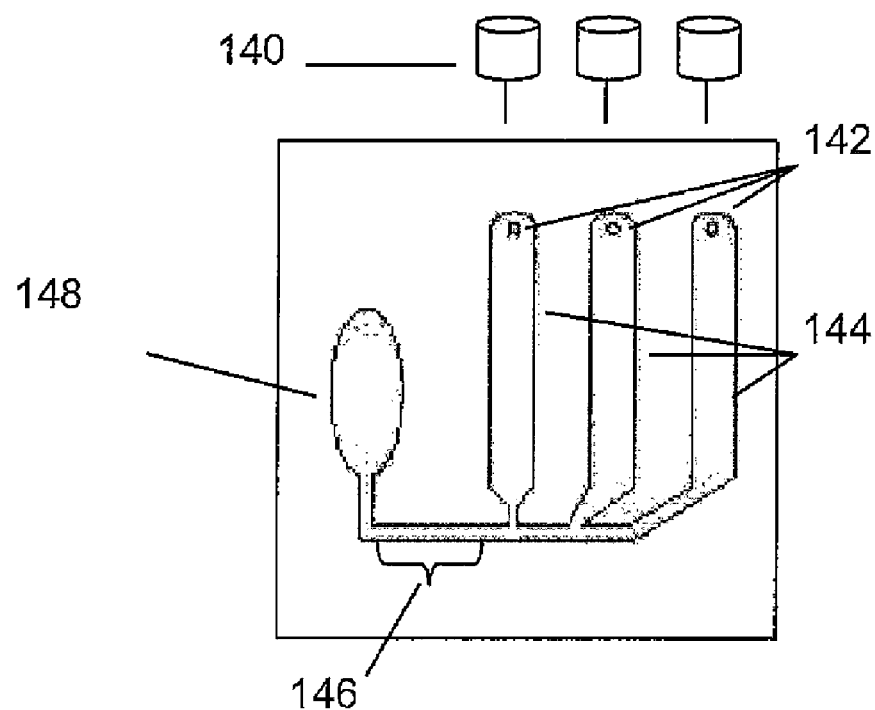
FIG. 8 is a diagram illustrating an automated microassay device according to a preferred embodiment of the present invention.

Another particularly advantageous application of the present invention is the development of automated microassays, either conducted in small vials (such as with Access® from Beckman Coulter) or on a bioassay chip. Such microassays are valuable in a wide range of disciplines including medical diagnostics (for example, cardiac biomarkers and metabolic health biomarkers) and environmental monitoring (for example, polynuclear aromatic hydrocarbons). Developing small, potentially portable assay devices is currently hindered by the large size, awkward shape, and power consumption requirements of existing pumps. These pumps are necessary in order to deliver reagents to produce the necessary reactions, implement wash steps, and mix reagents. In one embodiment of the present invention, a pump or pumps as disclosed herein may be employed to deliver reagents to specific container(s) as may be used for automated bioassay procedures. Examples of containers might be beakers, corvettes, small chambers, microtiter plates, etc. In this embodiment, reagents could be delivered either directly from the pump to the container or the pump could be used to hydraulically drive the reagent from a holding reservoir to the container. Either these same pumps or other pumps could also be used to mix reagents by oscillating flow forward then reverse, by delivering reagents at a higher rate of flow, by flowing gas bubbles through the solution, by hydraulically oscillating the container, or other similar methods. In another embodiment, a pump or pumps as disclosed herein may be employed within a bioassay chip to facilitate all steps of an automated assay. The pump sequence, reagent delivery volume and flow rate could be controlled/performed automatically by a small or hand-held device. Analyte detection could also be performed on the chip using the device. In another embodiment, the pump or pumps could be separate from the chip and contained within the device. Upon insertion of the chip into the device, needles could penetrate self-sealing septa on the chip and pumps automatically activated to deliver reagents on the chip (or within the device) to a detection region. One example is schematically represented in FIG. 8. In this example, upon insertion of the chip into the device, pumps with needle interface 140 will be brought into contact with the chip, piercing self-sealing septa 142. Pumps 140 can be activated in a sequence, for duration, and at a flow rate, determined by the specific assay steps to push the reagent or wash solution in reservoirs 144 to detection region 146. Alternatively, the pumps may contain the necessary reagents and deliver those reagents directly to detection region 146. Waste can be contained on the chip by means of expansion reservoir 148 that is made of material that can stretch to accommodate the expected volume of waste. Sample introduction may occur before insertion of the chip into the device or may be incorporated into the automated pumping sequence. Pumps 140 could also perform mixing of reagents and sample materials as described above as needed for specific assays.

As used herein, "comprising" is synonymous with "including," "containing," or "characterized by," and is inclusive or open-ended and does not exclude additional, unrecited elements or method steps. As used herein, "consisting of" excludes any element, step, or ingredients not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

When a Markush group or other grouping is used herein, all individual members of the group and all combinations and subcombinations possible of the group are intended to be individually included in the disclosure.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Thus, additional embodiments are within the scope of the invention and within the following claims.

In general the terms and phrases used herein have their art-recognized meaning, which can be found by reference to standard texts, journal references and contexts known to those skilled in the art. The preceding definitions are provided to clarify their specific use in the context of the invention.

All patents and publications mentioned in the specification are indicative of the levels of skill of those skilled in the art to which the invention pertains. All references cited herein are hereby incorporated by reference to the extent that there is no inconsistency with the disclosure of this specification.

We claim:

1. An electrochemical pump comprising an electrochemical cell, the electrochemical cell comprising:
   a) a first compartment comprising a first electrode and a first electrolyte solution, the first electrolyte solution comprising a first redox couple different in composition from the first electrode and which participates in a first electrode reaction and a first group of ions, wherein neither of the species of the first redox couple is a gas;
   b) a second compartment comprising a second electrode and a second electrolyte solution, the second electrolyte solution comprising a second redox couple different in composition from the second electrode and which participates in a second electrode reaction and a second set of ions, wherein neither of the species of the second redox couple is a gas; and
   c) an ion conducting separator separating the first and second compartment, the separator being in fluid communication with the first and second electrolyte solution, wherein the separator has an effective pore diameter of less than about 50 nm.

2. The electrochemical pump of claim 1, wherein the ion conducting separator comprises a membrane.

3. The electrochemical pump of claim 1, wherein said first group of ions is different from the first redox couple species, said second group of ions is different from the second redox couple species, and wherein the separator allows transport of at least some species of the first and second groups of ions but restricts transport of the ions of the first and second redox couples.

4. The electrochemical pump of claim 2, wherein the membrane has an effective pore diameter of less than about 20 nm.

5. The electrochemical pump of claim 4, wherein the membrane has an effective pore diameter of about 4 nm.

6. The electrochemical pump of claim 1, further comprising one of a heater and a cooler in thermal communication with one of the first and second compartments.

7. The electrochemical pump of claim 1, further comprising one of a complexing agent and a chelating agent within at least one of the first and second compartments capable of shifting a standard electrode potential of at least one of the first and second electrode reactions.

8. The electrochemical pump of claim 1, wherein at least one of the first and second redox couples comprises a second-stage redox couple in solution which participates in a second-stage reaction following one of the first and second electrode reactions.

9. The electrochemical pump of claim 8, wherein the second-stage redox couple comprises vanadium.

10. The electrochemical pump of claim 1, wherein the pump comprises a shape chosen from the group of stacked cylindrical, stacked disks, stacked rectangular, cylinder within cylinder, sphere within sphere, stacked sphere, V-shaped, and dumbbell-shaped.

11. The electrochemical pump of claim 10, wherein the pump is elongated and bendable to a desired shape.

12. The electrochemical pump of claim 10, wherein the pump is shaped to fit securely on an animal.

13. The electrochemical pump of claim 10, wherein the pump is shaped to be implantable in an organism.

14. The electrochemical pump of claim 1, further comprising a first flexible diaphragm in communication with the first compartment and a first fluid chamber, wherein the first flexible diaphragm separates the first compartment from the first fluid chamber.

15. The electrochemical pump of claim 14, further comprising a second flexible diaphragm in communication with the second compartment and a second fluid chamber, wherein the second flexible diaphragm separates the second compartment from the second fluid chamber.

16. The electrochemical pump of claim 15, further comprising a first fluid chamber inlet and outlet and a second fluid chamber inlet and outlet.

17. The electrochemical pump of claim 16, wherein at least one of the first fluid chamber inlet and outlet and at least one of the second fluid chamber inlet and outlet comprise a check valve.

18. The electrochemical pump of claim 16, further comprising a constant-volume solution application and a fluidic connection connecting the first and second fluid chambers, whereby a constant volume of a solution is present in the sum of the volumes of the solution present in the first and second fluid chambers, the application, and the fluidic connection.

19. The electrochemical pump of claim 1, further comprising a support structure supporting said separator.

20. The electrochemical pump of claim 19, wherein said support structure comprises a plurality of holes through which said first and second electrolyte solutions may contact said separator.

21. The electrochemical pump of claim 20, wherein said plurality of holes in said support structure are each about 3.2 mm in diameter.

22. The electrochemical pump of claim 20, further comprising a mesh structure sandwiched between said separator and said support structure.

23. The electrochemical pump of claim 22, wherein said mesh structure is a nylon mesh with a pore diameter of about 100 micrometers.

24. A selectively controllable valve, comprising:
   a) an electrochemical cell, the electrochemical cell comprising: a first compartment comprising a first electrode and a first electrolyte solution, the first electrolyte solution comprising a first redox couple different in composition from the first electrode and which participates in a first electrode reaction; a second compartment comprising a second electrode and a second electrolyte solution, the second electrolyte solution comprising a second redox couple different in composition from the second electrode and which participates in a second electrode reaction; and an ion conducting separator separating the first and second compartment;
   b) a fluid pathway in hydraulic communication with the electrochemical cell; and
   c) a flexible diaphragm in fluid communication with one of the first and second electrolyte solutions, wherein expansion of the flexible diaphragm in response to at least one of the first and second electrode reactions at least partially blocks the fluid pathway.

25. The valve of claim 24, wherein the ion conducting separator comprises a membrane.

26. A microfluidic chip, comprising:
   a) a first pumping fluid reservoir comprising a first electrode and a first electrolyte solution, the first electrolyte solution comprising a first redox couple different in composition from the first electrode and which participates in a first electrode reaction and a first group of ions, wherein neither of the species of the first redox couple is a gas;
   b) a second pumping fluid reservoir comprising a second electrode and a second electrolyte solution, the second electrolyte solution comprising a second redox couple different in composition from the second electrode and which participates in a second electrode reaction and a second set of ions, wherein neither of the species of the second redox couple is a gas;
   c) an ion conducting separator separating the first and second pumping fluid reservoirs, the separator being in fluid communication with the first and second electrolyte solution;
   d) a barrier in communication with the second pumping fluid reservoir;
   e) a pumping chamber adjacent the barrier and comprising a volume, the pumping chamber positioned such that expansion of the barrier decreases the volume of the pumping chamber; and
   f) a microfluidic channel connected to the pumping chamber, whereby expansion of the barrier causes a fluid within the pumping chamber to flow through the microfluidic channel.

27. The microfluidic chip of claim 26, wherein the ion conducting separator comprises a membrane.

28. The microfluidic chip of claim 26, wherein said first group of ions is different from the first redox couple species, said second group of ions is different from the second redox couple species, and wherein the separator allows transport of at least some species of the first and second groups of ions but restricts transport of the ions of the first and second redox couples.

29. The microfluidic chip of claim 26, wherein the barrier is one of a flexible diaphragm, a gas bubble, a solid plug, and an immiscible slug.

30. A microassay device, comprising:
   a) a first compartment comprising a first electrode and a first electrolyte solution, the first electrolyte solution comprising a first redox couple different in composition from the first electrode and which participates in a first electrode reaction and a first group of ions, wherein neither of the species of the first redox couple is a gas;
   b) a second compartment comprising a second electrode and a second electrolyte solution, the second electrolyte solution comprising a second redox couple different in composition from the second electrode and which participates in a second electrode reaction and a second set of ions, wherein neither of the species of the second redox couple is a gas;
   c) an ion conducting separator separating the first and second compartments, the separator being in fluid communication with the first and second electrolyte solution; and
   d) a reagent container in hydraulic communication with at least one of said first and second compartments.

31. The microassay device of claim 30, wherein the ion conducting separator comprises a membrane.

32. The microassay device of claim 30, wherein said first group of ions is different from the first redox couple species, said second group of ions is different from the second redox couple species, and wherein the separator allows transport of at least some species of the first and second groups of ions but restricts transport of the ions of the first and second redox couples.

33. The microassay device of claim 30, further comprising a holding reservoir in hydraulic communication with one of said first and second compartments and said container whereby a reagent may be delivered between said holding reservoir and said container.

34. The microassay device of claim 33, further comprising a detection region in hydraulic communication with said holding reservoir and said container.

35. The microassay device of claim 33, further comprising an expandable barrier between one of said first and second compartments and said holding reservoir.

36. The microassay device of claim 35, wherein said holding reservoir comprises a self-sealing septa, and the microassay device further comprising a needle providing a fluid passage from the expandable barrier to said holding reservoir.

37. The microassay device of claim 30, wherein said container is expandable.

* * * * *